(12) United States Patent
Collazo (10) Patent No.: US 7,547,327 B2
(45) Date of Patent: Jun. 16, 2009

(54) EXPANDABLE AUGMENT TRIAL

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 379 days.

(21) Appl. No.: 10/678,352

(22) Filed: Oct. 3, 2003

(65) Prior Publication Data

US 2005/0075736 A1    Apr. 7, 2005

(51) Int. Cl.
A61F 2/38      (2006.01)
(52) U.S. Cl. .................. 623/20.16; 623/20.35
(58) Field of Classification Search ............. 623/20.15, 623/20.16, 23.28, 18.11, 20.28, 20.29, 20.32, 623/20.33, 20.35, 22.42, 20 FOR, 20.14, 623/20.17, 20.19, 20.21, 20.22, 20.23, 20.24, 623/20.25, 20.26, 20.27, 20.3, 20.31, 20.36
See application file for complete search history.

(56) References Cited

U.S. PATENT DOCUMENTS

| | | | |
|---|---|---|---|
| 4,936,847 A | 6/1990 | Manginelli | |
| 5,147,406 A | 9/1992 | Houston et al. | |
| 5,152,796 A | 10/1992 | Slamin | |
| 5,181,925 A | 1/1993 | Houston et al. | |
| 5,226,915 A | 7/1993 | Bertin | |
| 5,258,032 A | 11/1993 | Bertin | |
| 5,326,359 A | 7/1994 | Oudard | |
| 5,405,395 A | 4/1995 | Coates | |
| 5,415,662 A | 5/1995 | Ferrante et al. | |
| 5,458,645 A | 10/1995 | Bertin | |
| 5,472,415 A | 12/1995 | King et al. | |
| 5,522,897 A | 6/1996 | King et al. | |
| 5,549,685 A | 8/1996 | Hayes | |
| 5,560,096 A | 10/1996 | Stephens | |
| 5,562,675 A | 10/1996 | Mc Nulty et al. | |
| 5,571,194 A * | 11/1996 | Gabriel | 623/20.16 |
| 5,609,645 A | 3/1997 | Vinciguerra | |
| 5,683,472 A | 11/1997 | O'Neil et al. | |
| 5,702,460 A | 12/1997 | Carls et al. | |
| 5,755,800 A | 5/1998 | O'Neil et al. | |
| 5,776,201 A | 7/1998 | Colleran et al. | |
| 5,879,393 A | 3/1999 | Whiteside et al. | |
| 5,885,296 A | 3/1999 | Masini | |
| 5,928,286 A | 7/1999 | Ashby et al. | |
| 5,944,722 A | 8/1999 | Masini | |
| 5,947,973 A | 9/1999 | Masini | |
| 5,957,926 A | 9/1999 | Masini | |
| 5,961,523 A | 10/1999 | Masini | |
| 5,967,523 A | 10/1999 | Brownlee | |
| 5,971,989 A | 10/1999 | Masini | |
| 5,984,969 A | 11/1999 | Matthews et al. | |
| 6,004,352 A * | 12/1999 | Buni | 623/20.33 |
| 6,063,091 A | 5/2000 | Lombardo et al. | |
| 6,068,633 A | 5/2000 | Masini | |
| 6,077,269 A | 6/2000 | Masini | |

(Continued)

FOREIGN PATENT DOCUMENTS

WO     WO 01/89428 A2 *   11/2001

*Primary Examiner*—David H. Willse
(74) *Attorney, Agent, or Firm*—Lerner, David, Littenberg, Krumholz & Mentlik, LLP (57) ABSTRACT

An expandable trial augment, a trial including an augment and a method for using an expandable trial augment are provided. The trial augment is preferably biased to expand in at least one direction.

21 Claims, 7 Drawing Sheets

U.S. PATENT DOCUMENTS

| | | |
|---|---|---|
| 6,096,082 A | 8/2000 | Stegmuller et al. |
| 6,102,916 A | 8/2000 | Masini |
| 6,159,217 A | 12/2000 | Robie et al. |
| 6,187,010 B1 | 2/2001 | Masini |
| 6,203,576 B1 | 3/2001 | Afriat et al. |
| 6,214,011 B1 | 4/2001 | Masini |
| 6,228,090 B1 | 5/2001 | Waddell |
| 6,299,645 B1 | 10/2001 | Ogden |
| 6,355,067 B1 * | 3/2002 | Bloebaum ................ 623/16.11 |
| 6,416,552 B1 | 7/2002 | Hoeppner et al. |
| 6,458,135 B1 | 10/2002 | Harwin et al. |
| 6,494,914 B2 | 12/2002 | Brown et al. |
| 6,494,915 B1 | 12/2002 | Gonzalez et al. |
| 6,503,254 B2 | 1/2003 | Masini |
| 6,984,249 B2 * | 1/2006 | Keller .................... 623/20.24 |
| 2001/0001120 A1 | 5/2001 | Masini |
| 2002/0082607 A1 | 6/2002 | Heldreth et al. |
| 2002/0120341 A1 | 8/2002 | Stumpo et al. |
| 2002/0138150 A1 | 9/2002 | Leclercq |
| 2003/0009230 A1 | 1/2003 | Gundlapalli et al. |
| 2004/0019353 A1 * | 1/2004 | Freid et al. .................... 606/69 |

* cited by examiner

EXPANDABLE AUGMENT TRIAL

FIELD OF THE INVENTION

The invention relates to trial augments used with femoral trials during knee surgery.

BACKGROUND OF THE INVENTION

Failure of a knee arthroplasty can be caused by a variety of factors, and such failure requires knee revision surgery. When a distal condylar defect is present during total knee replacement, the surgeon corrects this condition by preparing the defective bone to accept a femoral component implant that includes an augment. Typically, the distal end of the femur is resected to remove diseased or unhealthy bone to ensure sufficient anchoring and proper fit of the femoral component implant. Augments are used with the femoral component to increase the thickness of the inferior portion of the femoral component to compensate for lack of sufficient bone tissue. Thus, an augment is a spacer to fill a gap between the femoral component and the resected femur.

Trial components are used in knee replacement surgery to assist the surgeon in determining the appropriate size and type of femoral implant to use on a particular patient. A femoral trial is placed on a resected femoral surface and a tibial trial is placed on a prepared tibial surface. With the trials in place, the knee is checked for flexion and extension. Thus, during the trialing phase of the surgical procedure, the surgeon makes a final check of the reconstructed joint by temporarily inserting the trials, which mimic the final implants prior to permanent placement of the implant. Similar to the final implants, augments are used, particularly for the femoral trial, so that the surgeon can fill any voids and deficiencies between the inner surface of the trial and the resected femur.

Presently, trial augments having thicknesses between 2 mm and 20 mm are used with femoral trials. Typically, a set of trial augments are provided in a surgical tray having thicknesses of 5 mm and 10 mm, and in some cases, 5 mm, 10 mm, and 15 mm. In addition, the trial augments generally are provided in 8 different standard sizes that vary in length in the anterior-posterior direction and width in the medial-lateral direction to be used with various sized femoral trials. The distal femoral trial augments that are currently in use are specific to the size of the femoral trial component to be used. Since the final implant size selection is not made until the time of surgery, a large number of different sized trial augments have to be stored and available for use in a sterilized tray. It would be desirable to reduce the number of trial augments required for knee surgery.

SUMMARY OF THE INVENTION

In accordance with one or more embodiments of the present invention, an orthopaedic trial augment is provided comprising a first block and an expansion member. According to these embodiments, the expansion member is slidably associated with the first block so that the trial is expandable in at least one direction. The expansion member may include a second block. In one or more preferred embodiments, the first and second blocks are biased such that the blocks expand in at least one direction. Biasing may be accomplished by providing a spring associated with at least one of the blocks, and the spring configured to permit sliding movement between the blocks and expansion of the augment.

According to certain embodiments, one of the first or second blocks includes at least one channel and the other of the first or second blocks includes at least one complementary surface configured to provide sliding movement between the first and second blocks. According to some embodiments, one of the first or second blocks is keyed to fit inside the other of the first or second blocks to permit sliding movement between the two blocks in at least one direction. The keyed fitting structure may be provided wherein one of the first or second blocks includes at least a pair of grooves adapted to receive complementary surfaces on the other of the first or second blocks. In certain preferred embodiments, the trial expands in an anterior-posterior direction with respect to an orthopaedic trial.

According to some embodiments, the trial augment includes engagement surfaces configured to cooperate with at least one groove in an orthopaedic trial to secure the trial augment within the orthopaedic trial. The trial augment may further include a stop member to prevent the blocks from sliding apart. The stop member may include a pin or other suitable device to prevent the blocks from sliding apart. Other embodiments relate to a surgical tray including an orthopaedic trial augment of one of the embodiments described herein.

Another embodiment of the invention relates to an orthopaedic trial implant. The trial implant comprises a main trial implant body having at least one surface configured to be in contact with a bone surface and a recess in the main trial implant body adapted to receive a trial augment. The recess has at least one engagement surface for securing an augment in the recess. According to one embodiment, the engagement surface includes a groove. The trial implant further includes an expandable augment biased to expand in at least one direction and configured to be received in the recess. The expandable trial augment includes at least one edge surface configured to cooperate with the at least one engagement surface.

Still another embodiment of the invention relates to a method of augmenting an orthopaedic trial implant. The method comprises providing a trial implant having at least one recess and an engagement surface for a trial augment and inserting a trial augment in the recess, the trial augment being expandable in at least one direction. According to certain embodiments, the trial augment is compressed in at least one direction prior inserting the trial augment in the recess. In these embodiments, the trial augment is released after insertion in the recess, such that that the trial augment expands and is secured in the recess between the engagement surfaces. Preferably, the spring provides sufficient force to secure the block between the engagement surfaces.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF EXEMPLARY EMBODIMENTS

Before describing several exemplary embodiments of the invention, it is to be understood that the invention is not limited to the details of construction or process steps set forth in the following description. The invention is capable of other embodiments and of being practiced or carried out in various ways.

In overview, one or more embodiments of the invention relates to an expandable trial augment. Other embodiments relate to an orthopaedic trial implant using an expandable augment and a method of using an expandable augment trial. According to one or more embodiments of the invention, the number of trial augments needed during surgery is greatly reduced. As discussed above in the background section, there are generally at least eight different sized augments for the different sized trials, and in particular femoral trials, used in knee surgery. For each different size trial augment, at least two different thicknesses are usually provided in the surgical tray used by the surgeon performing the knee surgery. The present invention reduces the number of parts required in the surgical tray and simplifies the trialing procedure during knee revision surgery.

Figure 1:
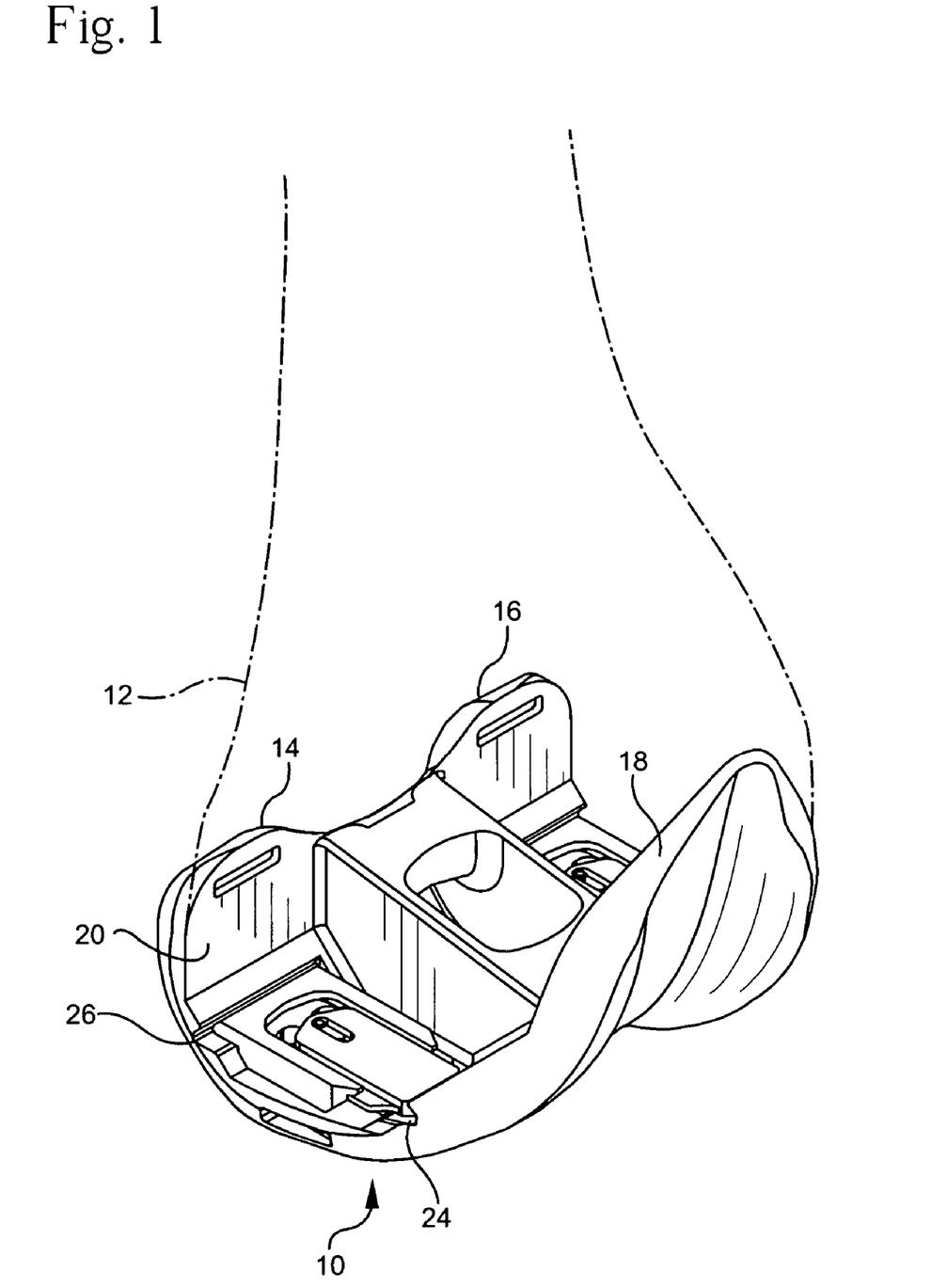
FIG. 1 is an assembled perspective view of a femoral trial with a pair of trial augments secured to the trial according to one embodiment of the present invention.
Figure 2:
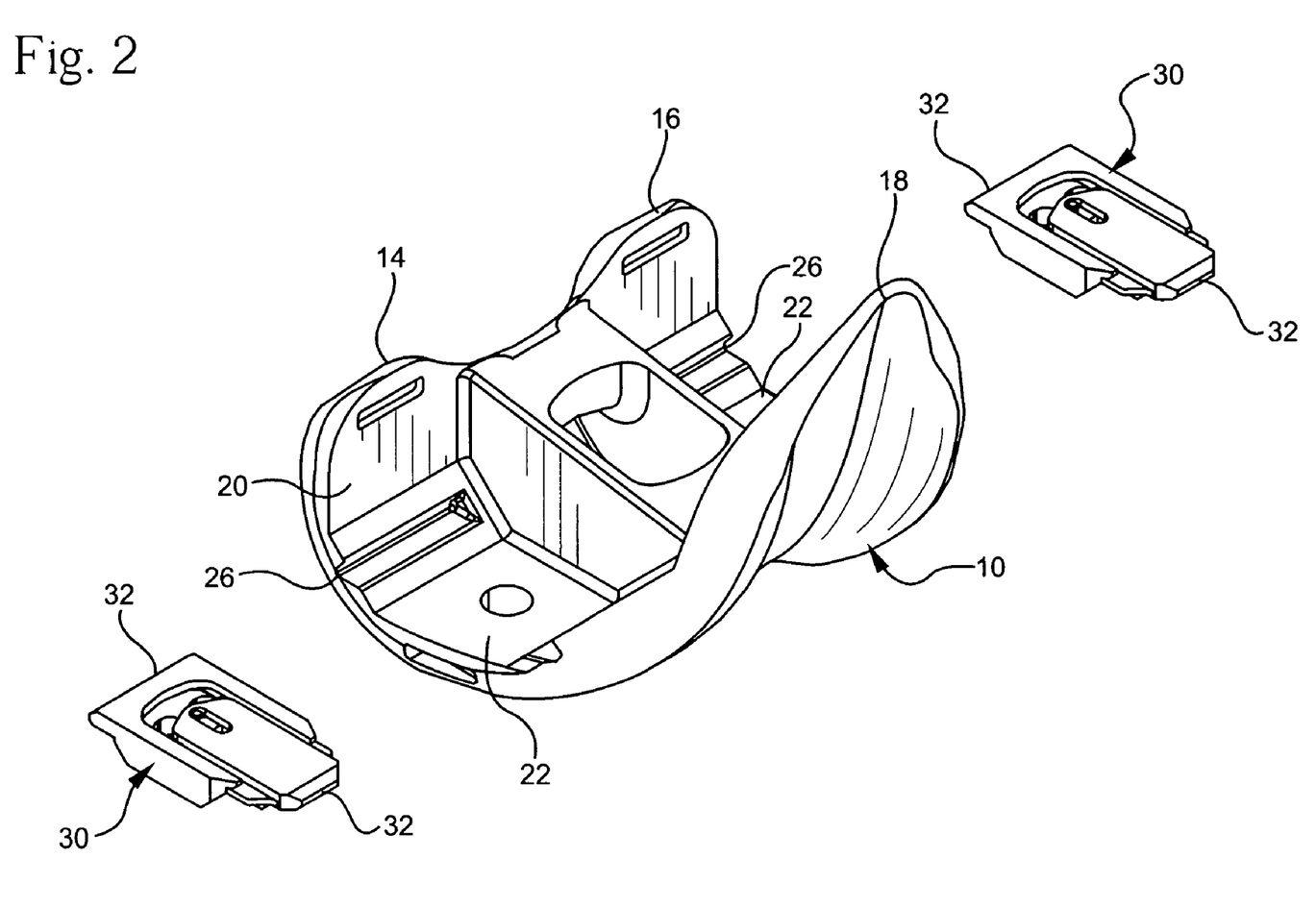
FIG. 2 is an exploded perspective view of a femoral trial according to one embodiment of the invention.
Figure 3:
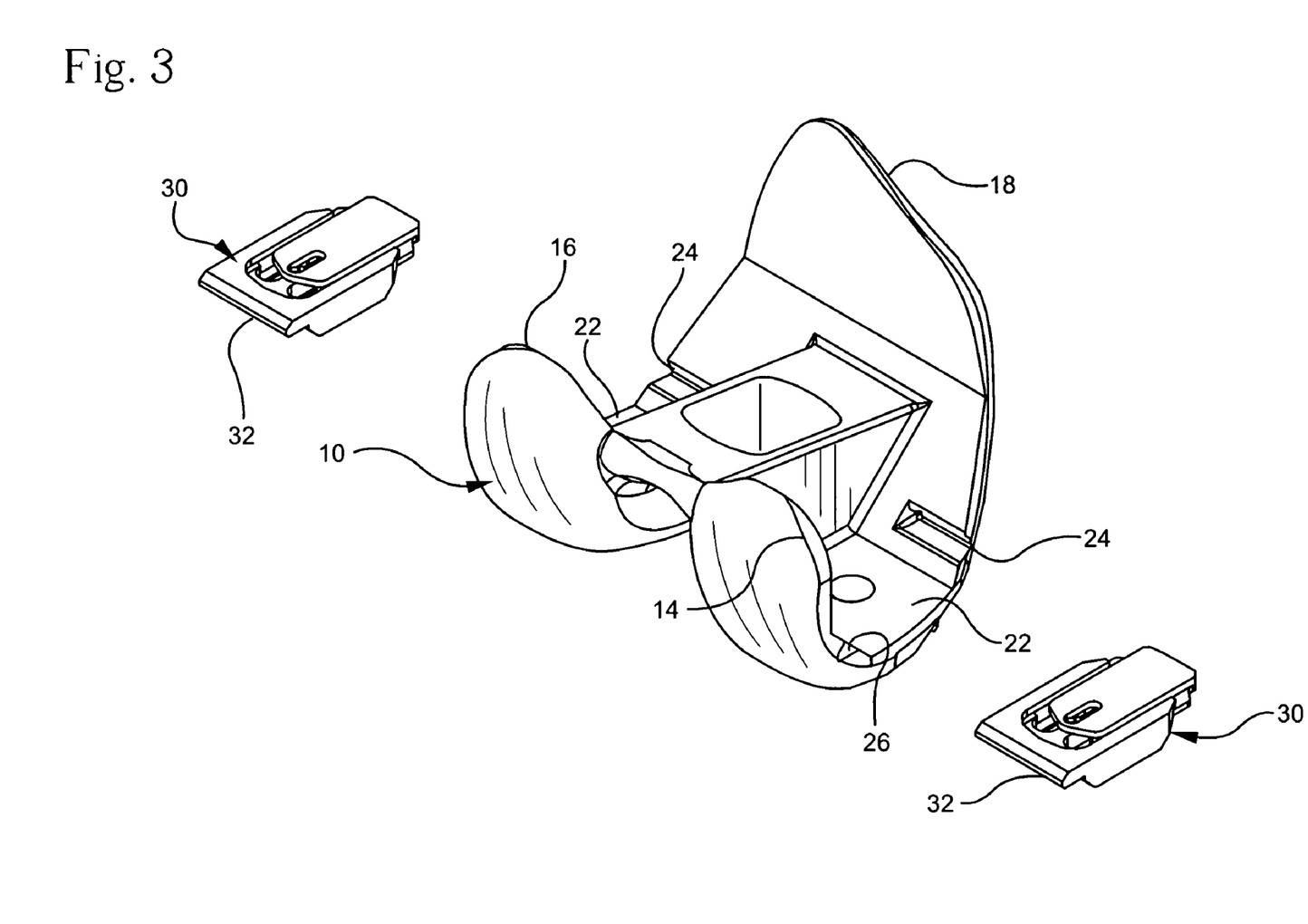
FIG. 3 is an exploded perspective view of a femoral trial according to one embodiment.

Referring to the drawings and first to FIGS. 1-3, an orthopaedic trial implant, and in particular, a femoral trial implant 10 is shown. In FIG. 1, the trial implant 10 is shown mounted to the distal end of a femur 12 (shown in phantom). As is known in the art, the femoral trial implant 10 includes a pair of condyles 14, 16, and an anterior flange 18. The anterior flange 18 covers an anterior portion of the femur and the condyles 14, 16 cover a posterior portion of the femur when the trial implant 10 is mounted to the distal end of a femur in a known manner. According to one or more embodiments, a trial implant 10 is provided comprising a main trial implant body 10 having at least one surface 20 configured to be in contact with a bone surface, and in particular, a distal end of the femur 12. At least one recess, but typically two recesses 22 are provided in the main trial implant body adapted to receive a trial augment 30. The trial implant body 10 has at least one engagement surface 24 associated with each recess 22 for securing a trial augment 30 in the recess 22. In preferred embodiments, the engagement surface 24 is in the form of a slot or groove that cooperates with an end surface 32 on one end of the trial augment 30. Each recess 22 may include a pair of engagement surfaces 24, 26 for securing an augment in each recess 22. The end surface 32 preferably has a shape that is complementary and cooperates with the engagement surface 24. In the embodiment shown, the end surface 32 has a beveled or pointed end that fits in the engagement surfaces 24, 26.

The augment 30 is preferably an expandable augment that is biased to expand in at least one direction and configured to be received in the recess 22, as will be described in more detail below. In preferred embodiments, the expandable trial augment 30 comprises a pair of slidingly engaged blocks having a spring disposed between the blocks so that the augment expands in at least one direction. According to certain preferred embodiments, the blocks include keyed mating surfaces permitting sliding movement between the two blocks. These features will be described in more detail below. Preferably, the augment 30 is made from a material that can be autoclaved and reused. Such autoclavable materials are known in the art. However, the present invention is not limited to a particular material to construct the augment 30.

Referring now to FIGS. 4-8, according to one or more embodiments an orthopaedic trial augment 30 comprises at least a first block 34 and an expansion member 36 slidably associated with the first block so that that the trial 30 is expandable in at least one direction. Preferably, the expansion member 36 includes a second block. In highly preferred embodiments, the first block 34 and the expansion member 36 are biased such that the blocks 34, 36 expand in at the least one direction. In the embodiments shown, the augment 30 expands in an anterior-posterior direction with respect to the trial implant. In other embodiments, the augment may expand in the medial-lateral direction with respect to the trial implant. Still in other embodiments, the augment may expand in both the anterior-posterior and medial-lateral directions. The first block 34 and the expansion member 36 can be biased to slide apart to expand the trial augment 30 by a spring 38 associated with at least one of the blocks.

Figure 4:
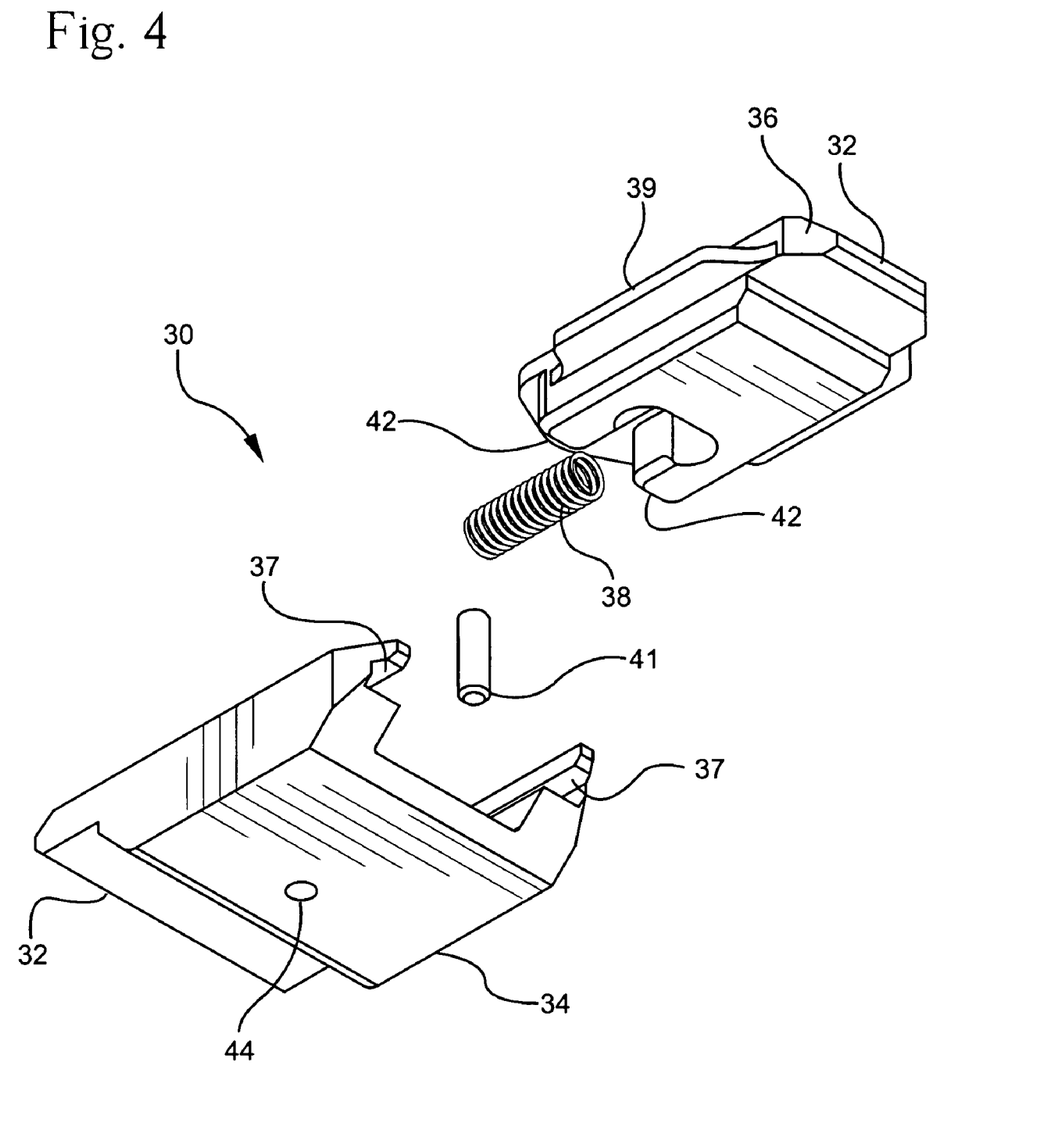
FIG. 4 is an exploded perspective view of a trial augment according to one embodiment.
Figure 5:
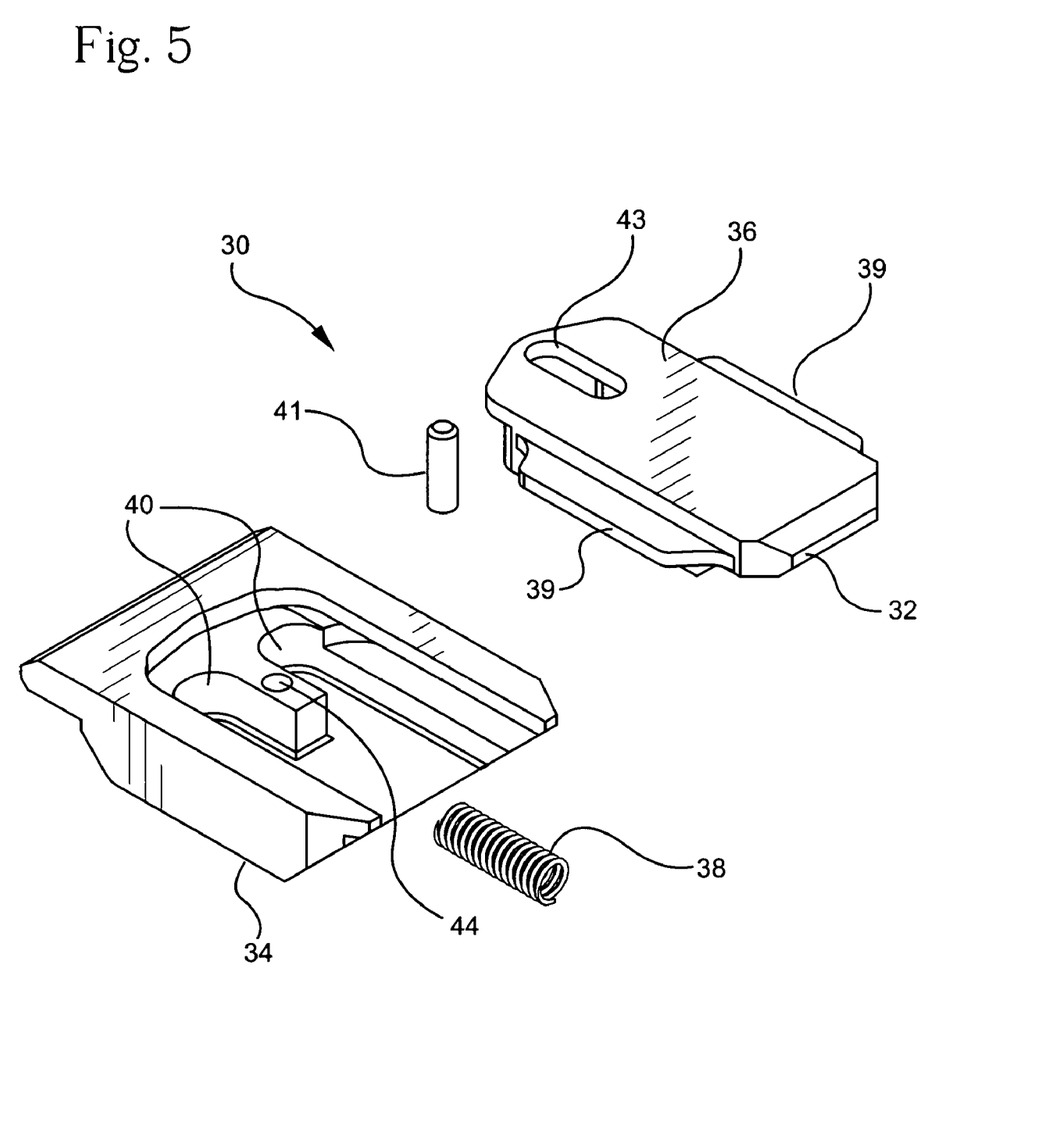
FIG. 5 is an exploded perspective view of a trial augment according to one embodiment.
Figure 6:
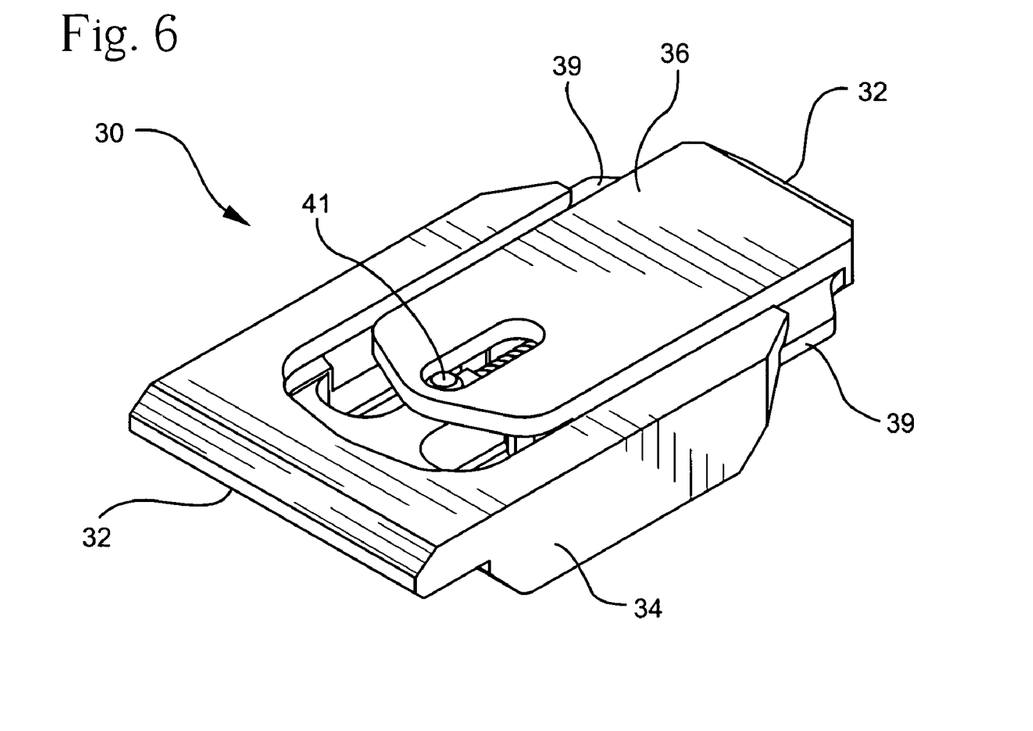
FIG. 6 is an assembled perspective view of a trial augment according to one embodiment.
Figure 7:
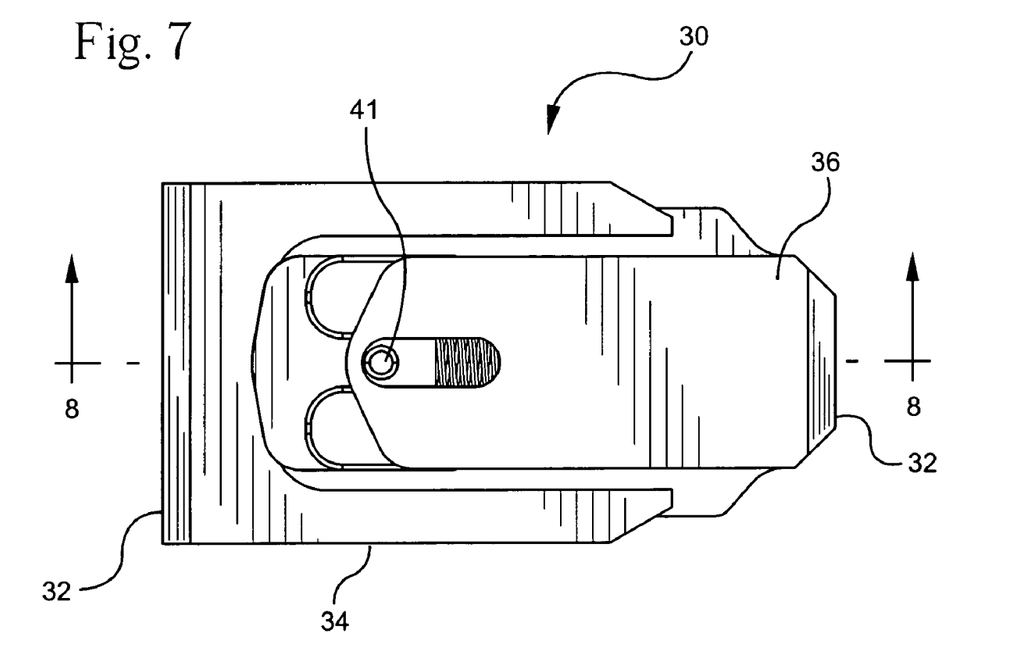
FIG. 7 is a top plan view of a trial augment according to one embodiment.

According to preferred embodiments, one of the first or second blocks includes at least one channel and the other of the first or second blocks includes at least one complementary surface configured to provide sliding movement between the first and second blocks. As shown in FIGS. 4 and 5, the first block includes a pair of channels 40 and the second block 36 includes a pair of complementary surfaces or rails 42 that slidingly engage the channels 40. In the embodiments shown in FIGS. 4 and 5, the blocks are keyed with complementary channels and rails to fit together to permit sliding movement between the two blocks in at least one direction, permitting the trial augment 30 to expand in at least the anterior-posterior direction with respect to the trial implant.

It will be understood that the above described configuration is just one example of a configuration that permits sliding movement between the first block 34 and the expansion member 36. Other designs can be used. For example, instead of a pair of channels 40 on the first block, a single channel or groove can be provided in either of the first or second blocks, and a single complementary rail can be provided to permit sliding movement between the blocks.

The trial augment 30 includes edge surfaces 32 configured to cooperate with at least one of the engagement surfaces or grooves 24, 26 in the orthopaedic trial implant 10 to secure the trial augment within the orthopaedic trial. The edge surfaces 32 may be beveled or pointed so that they fit securely in the engagement surfaces or grooves 24, 26. In certain embodiments, the trial augment 30 includes a stop member to prevent the blocks from sliding completely apart and prevent disassembly of the augment 30. The stop member may include a pin 41 or other suitable structure for preventing the blocks from sliding apart and disassembling. The pin 41 may cooperate with a track 43 in one of the blocks. As best shown in FIGS. 5-8, the pin 41 may be secured to the first block 34, for example, by inserting the pin 41 in an appropriately sized hole 44 in the first block 34. As best shown in FIGS. 6-9, when the pin 40 is seated in hole 44 of the first block 34 and the blocks 34 and 36 are assembled, the pin 41 and the track 43 cooperate to prevent the blocks from sliding completely apart.

In a fully assembled configuration, the spring 38 is seated between the channels 40 in the first block 34, and the second block 36 slides along the rails 42 in the channels 40. In preferred embodiments, the first block may include side channels 37 and the second block 36 may include side rails 39 to facilitate relative sliding movement between the two blocks 34, 36 and expansion of the trial augment 30. It will be understood, that in certain embodiments, either the side channels 37 and side rails 39 may be eliminated, or the channels 40 and rails 42 may be eliminated. In other words, only one set of channels and rails may be required to hold the blocks together and provide relative sliding movement between the blocks.

The trial augments described above are preferably used with femoral trial implants. The trial augments can be included as part of a kit or surgical tray used by a surgeon during knee revision surgery. Such a tray may include an orthopaedic implant trial and other components and tools needed for a knee revision surgery.

Figure 8:
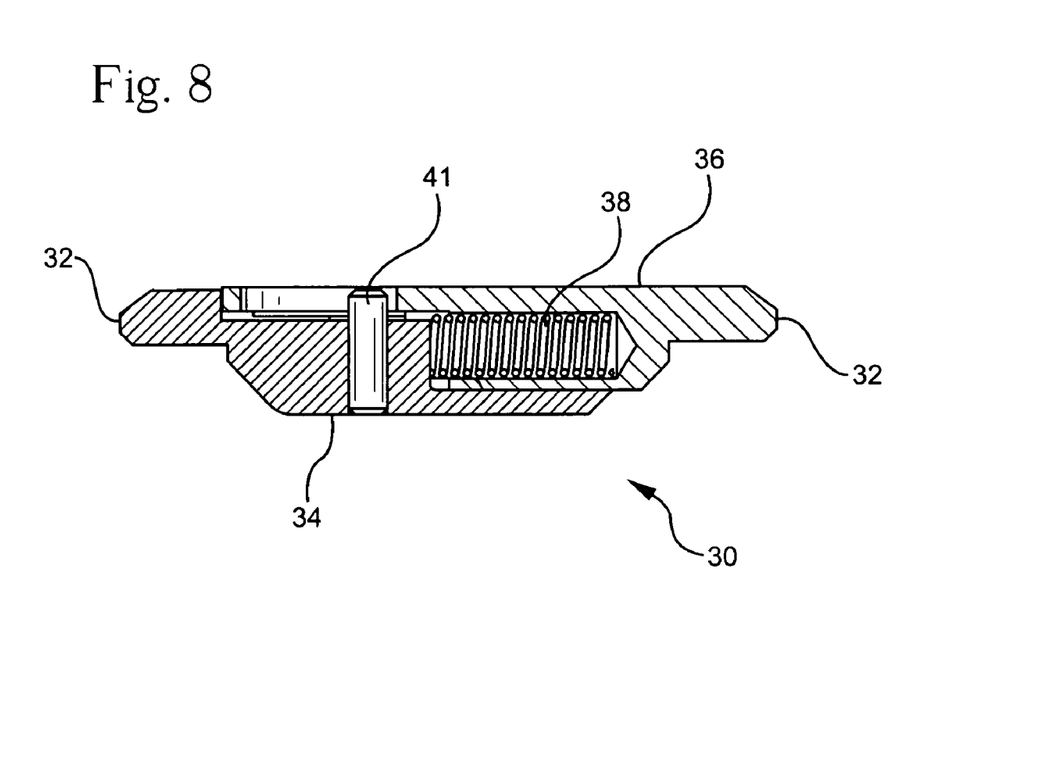
FIG. 8 a cross-sectional view taken along line 8-8 of FIG. 7 of the trial augment in the compressed position.
Figure 9:
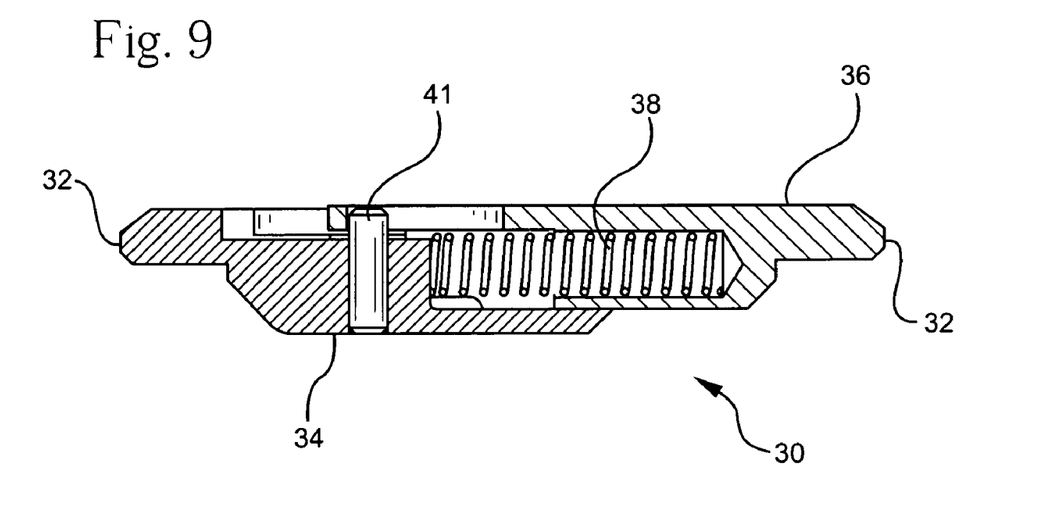
FIG. 9 a cross-sectional view taken along line 8-8 of FIG. 7 of the trial augment in an expanded position.

Another embodiment of the invention relates to a method of augmenting an orthopaedic trial implant. According to one or more embodiments, the method comprises providing a trial implant 10 of the type described above. The trial implant preferably has at least one recess 22 and an engagement surface for a trial augment 30. A trial augment 30 that is expandable in at least one direction, preferably the anterior posterior direction with respect to the trial implant, is then inserted in the recess of the trial implant. According to some embodiments, the trial augment 30 is compressed in at least one direction, as shown in FIG. 8, prior to inserting the trial augment in the recess. The trial augment 30 can be compressed by applying force to the ends of the first and second blocks 34, 36 causing the dimension of the trial augment 30 to decrease in at least one direction. The trial augment 30 is then placed in a recess 22 in the trial implant, and when the trial augment is released after insertion in the recess 22, the trial augment expands as shown in FIG. 9 and is secured in the recess between the engagement surfaces 24, 26, as best seen in FIG. 1. The spring 38 biases the blocks apart and provides sufficient force to secure the block between the engagement surfaces.

During a knee revision surgery, the surgeon would prepare the femoral and tibial surfaces by making the appropriate cuts to the bone surfaces using known surgical protocols, and then the femoral and tibial trials would be put in place to check for proper flexion and extension of the joint as is known in the art. Depending on the amount of bone cut from the distal end of the femur, augments having thicknesses between about 2 mm and 20 mm are used to fill any voids between the distal end of the femur and the femoral trial to determine the thickness of the augment to be used in the permanent femoral implant.

When the surgeon checks for flexion and extension with the trials in place, if the augment is too thin, during the check of flexion and extension, the joint will feel unstable or wobbly to the surgeon. In such instances, the femoral trial will be removed, and the trial augment will be compressed to remove the trial augment from the femoral trial implant. A thicker trial augment will then be inserted in the femoral trial implant, and the femoral trial implant will be assembled to the knee again. Flexion and extension is again checked by the surgeon. If the trial augment is too thick, the surgeon will not be able to move the knee joint from a flexed position to the extended position. If the leg cannot be straightened, the femoral trial is removed, the trial augment is removed, and a thinner trial augment is inserted in the femoral trial implant. This process is repeated until the surgeon determines that a proper fit has been achieved with the trial implants. Once a proper fit is achieved, the trial implants are removed, and the permanent implants are implanted in the femur and tibia.

Although the invention herein has been described with reference to particular embodiments, it is to be understood that these embodiments are merely illustrative of the principles and applications of the present invention. For example, the positioning of the channels and rails on the respective first and second blocks can be reversed. In addition, other stop structures can be used to prevent the augment from sliding completely apart. It is therefore to be understood that numerous modifications may be made to the illustrative embodiments and that other arrangements may be devised without departing from the spirit and scope of the present invention as defined by the appended claims and their equivalents.

What is claimed is:

1. An assembly comprising:
   a femoral trial implant including a condylar portion having an articular surface and a bone-facing cavity and;
   an orthopaedic trial augment for engaging the bone-facing cavity in the condylar portion of the femoral trial implant component, the orthopaedic trial augment comprising:
   a first block including at least one channel;
   a second block including at least one complementary surface for at least partial reception in the at least one channel of the first block to provide for sliding movement between the first and second blocks; and
   an expansion member directly connected with the first block and the second block so that the trial augment is expandable in at least one direction,
   wherein the first and second blocks are sized to engage the bone-facing cavity, form a substantially flat bone-facing surface which is coplanar with a bone surface, and are biased such that the blocks expand in the at least one direction.

2. The assembly of claim 1, wherein the expansion member is a spring configured to bias the blocks in opposite directions and expand the trial augment.

3. The assembly of claim 1, wherein one of the first or second blocks is keyed to fit inside the other of the first or second blocks to permit sliding movement between the two blocks in at least one direction.

4. The assembly of claim 3, wherein one of the first or second blocks includes at least a pair of grooves adapted to receive complementary surfaces on the other of the first or second blocks.

5. The assembly of claim 4, wherein the trial augment expands in an anterior-posterior direction with respect to the femoral trial implant.

6. The assembly of claim 5, wherein the trial augment includes engagement surfaces configured to cooperate with at least one groove in the bone-facing cavity of the femoral trial implant to secure the trial augment within the femoral trial implant.

7. The assembly of claim 6, further comprising a stop member to prevent the blocks from sliding apart.

8. The assembly of claim 7, wherein the stop member includes a pin.

9. A surgical tray including a femoral trial implant and an orthopaedic trial augment according to claim 1.

10. The assembly of claim 1, wherein the femoral trial implant includes first and second condylar portions, the first condylar portion having a first articular surface and a first bone-facing cavity and the second condylar portion having a second articular surface and a second bone-facing cavity.

11. The assembly of claim 10, further comprising first and second orthopaedic trial augments.

12. An assembly comprising:
   a femoral trial implant including a condylar portion having an articular surface and a bone-facing cavity and;
   an orthopaedic trial augment for engaging the bone-facing cavity in the condylar portion of the femoral trial implant component, the orthopaedic trial augment comprising:

a first block having an end portion for engaging an anterior end of the cavity in the condylar portion;

a second block having an end portion for engaging a posterior end of the cavity in the condylar portion, the second block keyed to fit inside the first block to permit sliding movement between the two blocks in at least one direction;

a spring element directly engaging the first and second blocks for moving the ends of the first and second blocks into biased engagement with the anterior and posterior ends of the cavity; and at least one of the first and second blocks having a substantially flat and proximally facing bone contacting surface which is coplanar with a bone surface, wherein first and second blocks are sized to engage the bone-facing cavity.

13. The assembly of claim 12, wherein one of the first or second blocks includes at least one channel and the other of the first or second blocks includes at least one complementary surface configured to provide sliding movement between the first and second blocks.

14. The assembly of claim 12, wherein one of the first or second blocks includes at least a pair of grooves adapted to receive complementary surfaces on the other of the first or second blocks.

15. The assembly of claim 14, wherein the trial augment expands in an anterior-posterior direction with respect to the orthopaedic trial.

16. The assembly of claim 15, wherein the trial augment includes engagement surfaces configured to cooperate with at least one groove in the bone-facing cavity of the femoral trial implant to secure the trial augment within the femoral trial implant.

17. The assembly of claim 16, further comprising a stop member to prevent the blocks from sliding apart.

18. The assembly of claim 17, wherein the stop member includes a pin.

19. A surgical tray including a femoral trial implant and an orthopaedic trial augment according to claim 12.

20. The assembly of claim 12, wherein the femoral trial implant includes first and second condylar portions, the first condylar portion having a first articular surface and a first bone-facing cavity and the second condylar portion having a second articular surface and a second bone-facing cavity.

21. The assembly of claim 20, further comprising first and second orthopaedic trial augments.

* * * * *